US006939336B2

(12) United States Patent
Silfver

(10) Patent No.: US 6,939,336 B2
(45) Date of Patent: Sep. 6, 2005

(54) METHOD AND DEVICE FOR TREATING INTER ALIA THE CERVIX

(76) Inventor: Violetta Silfver, Norrtullsgatan 16 B, 5 tr, SE-113 45 Stockholm (SE)

( * ) Notice: Subject to any disclaimer, the term of this patent is extended or adjusted under 35 U.S.C. 154(b) by 344 days.

(21) Appl. No.: 09/930,143

(22) Filed: Aug. 16, 2001

(65) Prior Publication Data

US 2002/0055706 A1 May 9, 2002

Related U.S. Application Data

(60) Provisional application No. 60/225,670, filed on Aug. 16, 2000.

(51) Int. Cl.$^7$ .............................................. A61M 31/00
(52) U.S. Cl. ....................................... 604/515; 128/898
(58) Field of Search ............................... 604/514, 515, 604/517; 128/898

(56) References Cited

U.S. PATENT DOCUMENTS

| | | | | |
|---|---|---|---|---|
| 3,903,265 A | * | 9/1975 | Meisch | 424/616 |
| 4,430,076 A | | 2/1984 | Harris | |
| 4,611,602 A | | 9/1986 | Bolduc | |
| 5,035,883 A | * | 7/1991 | Witkin | 424/78.07 |
| 5,052,382 A | * | 10/1991 | Wainwright | 128/202.25 |
| 5,098,415 A | * | 3/1992 | Levin | 604/293 |
| 5,364,375 A | | 11/1994 | Swor | |
| 5,797,872 A | * | 8/1998 | Ogata et al. | 604/500 |
| 5,951,511 A | * | 9/1999 | Lowder | 604/73 |
| 5,980,534 A | | 11/1999 | Gimpelson | |
| 6,028,104 A | * | 2/2000 | Schmidt et al. | 514/557 |
| 6,139,538 A | | 10/2000 | Houghton et al. | |
| 6,520,982 B1 | * | 2/2003 | Boynton et al. | 607/104 |
| 6,620,379 B1 | * | 9/2003 | Piuk et al. | 422/3 |
| 2003/0195481 A1 | * | 10/2003 | Xu et al. | 604/275 |

FOREIGN PATENT DOCUMENTS

| | | | |
|---|---|---|---|
| GB | 2334676 | * | 9/1999 |
| WO | WO 90/01957 | | 3/1990 |
| WO | WO 95/08363 | | 3/1995 |

* cited by examiner

*Primary Examiner*—Corrine McDermott
*Assistant Examiner*—Thomas J Sweet
(74) *Attorney, Agent, or Firm*—Birch, Stewart, Kolasch & Birch, LLP

(57) ABSTRACT

A non-invasive method for treating cells affected by at least one oncogenic virus is disclosed, comprising providing a substance comprising at least one of ozone, an ozone donor, oxygen and an oxygen donor; and subjecting the body tissue comprising the affected cells to the substance. The method is applied in the uterus cavity or uterine tubes for treating cells infected by pathologic viruses, bacteria or fungi. The device comprises a cup, having a bottom and a wall, and a shaft connected at one end to the bottom. The wall and shaft respectively extend in opposite directions from the bottom. The shaft has at least one inlet duct and at least one outlet duct. The wall has a mouth portion arranged to encircle the portio of the cervix uteri, and a chamber is defined by the bottom, wall and portio. The outlet duct(s) has at least one opening within the chamber.

15 Claims, 9 Drawing Sheets

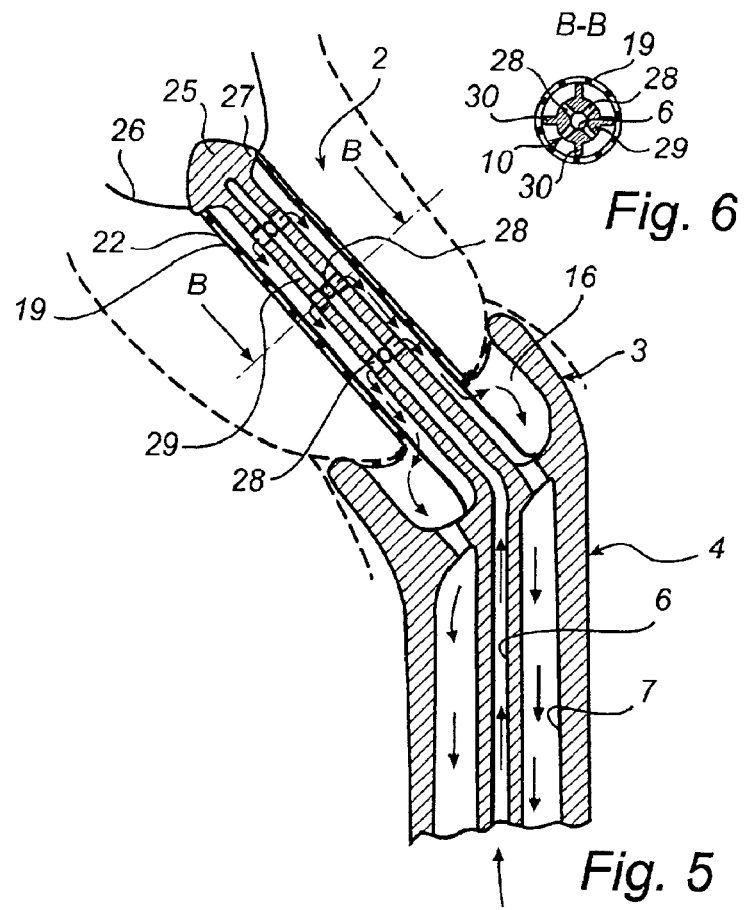
Fig. 6
Fig. 5
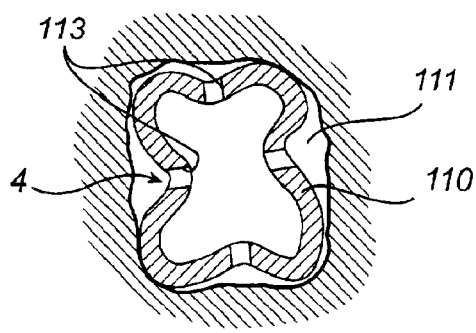
Fig. 11
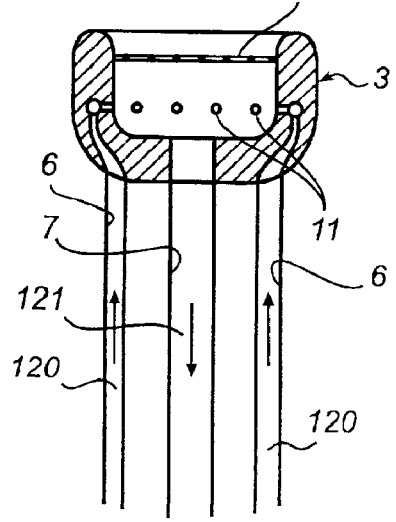
Fig. 12

METHOD AND DEVICE FOR TREATING INTER ALIA THE CERVIX

This application claims the benefit of provisional application No. 60/225,670, filed Aug. 16, 2000.

TECHNICAL FIELD

This invention relates to a method for treating the cervix uteri, and other portions of the body where cells can be affected by oncogenic viruses. In particular the invention relates to a method for treating cervix cancer. Further this invention relates to a device for performing the method and related actions at least in the cervix area.

TECHNICAL BACKGROUND

Cervix carcinoma is the third most common cancer among women worldwide. Approximately, 80% of all cervical malignancies are histologically squamous cell carcinomas. Experimental and epidemiologic data suggest that certain subtypes of human papilloma virus play an etiologic role in the development of cervical carcinoma by transforming epithelial cells into precancerous cells. The precancerous lesions may be defined as mild, moderate and severe dysplasia or carcinoma in situ. Studies have suggested that cancers in situ, when left untreated, can progress into invasive cancer after a varying period of time, up to several years. Despite intensive research during recent years, there is no available method to convenient and effectively treat women with cervical carcinoma without exposing the woman to expensive and invasive surgery.

Today there are at least three surgical or semi-surgical methods for removing affected cells in use. If possible the dysplastic cells are removed by either burning them off with a laser or by freezing them. In more severe cases traditional surgery is performed. In the latter case, a so called conicing is performed, where a cone of tissue is removed. The base of the cone is situated at the end of the cervix and the top of the cone is placed at a distance up the cervical canal. The conicing, due to the widening of the cervical canal and the weakening of the surrounding muscles, can cause secondary effects, such as chronic cervix insufficiency, bleeding, disordered menstruation period, and infertility.

The methods of freezing and burning are also surgical in that cells are actually mechanically removed. Since they are mainly used at an earlier state than the cutting surgery the amount of tissue removed is substantially less. However, a treatment having a surgical character is always accompanied by risks that do not exist in non-surgical treatments.

SUMMARY OF THE INVENTION

It is a primary object of this invention to provide a precise non-surgical method for treating affected cells in the cervix area, and a device for performing the method.

This object is achieved by a method and a device respectively according to the claims.

In one aspect thereof the present invention provides for a non-invasive method for treating cells affected by at least one oncogenic virus, comprising the steps of:
  providing a substance comprising at least one of ozone, an ozone donor, oxygen and an oxygen donor; and
  subjecting an area of body tissue comprising said affected cells to said substance.

As is evident from the definition of the method it is applicable not only for treating affected cells of the cervical area but for treating cells affected by an oncogenic virus in general. Oncogenic viruses can invade cells in various portions of the body including, but not limited to, the cervix, the vagina, the rectum, and the larynx. It is to be noted that the expression "cells which are affected by an oncogenic virus", for the purposes of this application, is to be interpreted as encompassing cells that are affected in any way by an oncogenic virus. Thus, "affected cells" includes all types of normal cells that are infected with oncogenic viruses, all grades of precancerous cells that have become precancerous because of such an infection, and all grades and kinds of cancerous cells resultant from such a precancerous stage. According to this invention the therapeutic agent of the substance is either ozone or oxygen or any combination thereof, where the ozone/oxygen can be provided in any appropriate form, such as in a free form, such as for example in a gaseous mixture, solved in a liquid, held in a solid substance, or a suspension, or being generated from a donor. In this context it is to be noted that "therapeutic" relates to a treatment of a developed state of illness as well as a prophylactic treatment. By "donor" is meant any chemical species that is able to donate the therapeutic agent, i.e. ozone or oxygen, to another species, which here is located in the affected cell. A man skilled in the art is capable of choosing appropriate donors according to principles known per se.

The method is advantageous for treating cervix uteri, and other organs, where oncogenic viruses undoubtly or at least most likely are capable of causing cell changes and cancer. In particular, the method is applicable for the treatment of cells affected by Human papilloma virus, which inter alia is responsible for the above described hitherto employed surgical methods for treating precancer stages of cancer and cancer in the cervix uteri. It is to be noted that the method of this invention could be used not only for treatment but for scientific purposes as well.

According to an advantageous embodiment of the method the step of subjecting comprises the steps of guiding said substance to said area, treating said affected cells by means of said substance, and guiding used substance away from said area. In this embodiment, for example, the treatment substance at the area can be continuously exchanged with fresh unused substance. This exchange can be achieved by actively pumping as well as by passively leading the substance away from the affected area.

According to another embodiment of the method a further step of desiccating said affected cells by means of said substance is performed. In this step preferably a gaseous substance consisting of dry gas is used for the treatment. By desiccating the cells it may be possible to obtain additional positive effects, because the desiccation causes unfavourable conditions for the viruses.

Further, the method is primarily adopted to the treatment of epithelial cells in cervix uteri. They constitute the surface of the tissue where they are arranged in one or more layers. It is also these cells in cervix uteri that become infected by oncogenic viruses, and thus the method is most effective for the aimed at treatment.

In yet another embodiment of the method according to the present invention there is provided the further steps of providing a substance holder with said substance, and positioning said substance holder at said area. This embodiment is useable for liquid and solid substances and mixtures thereof. By means of the once positioned holder the patient, for example, may get a greater freedom of movement. Further, treatments of long durability may be enhanced.

It is advantageous to monitor and control parameters indicating the status of the treatment and how it proceeds, in order to be able to make adjustments thereof, if necessary.

The monitoring and controlling are also used for keeping said parameters steady. The parameters can be of various types, such as chemical, biochemical, biological, physical, and microbiological.

As regards the durability and repetitiveness of the treatment these factors will be determined from case to case in dependence of the problem that is to be treated in each case. Thus, for example, the treatment can be anything from continuous to intermittent.

In another aspect of the present invention there is provided a method for non-invasive treatment of cells infected by at least one of pathologic viruses, bacteria and fungi in uterus cavity and uterine tubes. This method comprises the steps of providing a substance comprising at least one of ozone, an ozone donor, oxygen and an oxygen donor; and subjecting at least an area of said uterus cavity and uterine tubes comprising said affected cells to said substance. Thus the same operational steps are performed as in the previously described aspect, though applied to the uterus cavity and uterine tubes, where said pathologic viruses, bacteria or fungi cause chronic and persistent infections, which in some cases can lead to infertility.

The introduction of oxygen and/or ozone, even a very small amount, may promote the formation of free radicals that reduce the effect of harmful viruses in the cells. The increase in the oxygen level in the local blood vessels may activate the white blood cells so that the local immune system becomes more active. The increase in oxygen level may have a positive effect on the activity on macrophages that eliminate inflammations of tissues nearby affected cells, which inflammations are typically accompanying the process of tumor development.

Ozone has been used for different treatments. In recent years ozone has been used to inactivate inter alia viruses, as disclosed in for example U.S. Pat. Nos. 6,027,688 and 5,260,342. Primarily, the treatments have been directed to the treatment of blood, either inside of the body by introducing or having the patient inhale, etc. an ozone composition, such as disclosed in U.S. Pat. No. 5,260,342 or by leading the blood out of the body and into a machine and back into the body, such as in U.S. Pat. No. 6,027,688. However the method of subjecting cells affected by an oncogenic virus to ozon, in accordance with the present invention, has not been previously disclosed. A specific advantage of the present method is that it has the capability of eliminating the need of surgery when it comes to the treatment of cervix cancer, and also has the capability of preventing the development of cancer.

In another aspect thereof the present invention provides for a device arranged to be positioned at the cervix uteri of a human body, the device comprising a cup, having a bottom and a wall attached to said bottom and extending therefrom, and a shaft connected at one end thereof to the bottom and extending in an opposite direction of the wall, said shaft comprising at least one inlet duct and at least one outlet duct, said wall having a mouth portion arranged to encircle the portio of the cervix uteri, and the height of the wall being such that, when the device is disposed at the cervix uteri, a chamber is defined by said bottom, said wall and said portio, said outlet duct having at least one opening within said chamber.

For the purposes of this application it should be noted that the cervix uteri, which below will also be called merely cervix, is the lower portion of the uterus, that is a constricted neck which distends during parturition. The cervix uteri ends with the portio, which extends into the upper portion of the vagina. The formix vaginae, or formix cavity, is the upper end of the vagina which borders on the base of the portio. In other words the formix vaginae is a vault of the vagina, which encircles the portio at the base thereof. The mouth of the wall is arranged to encircle the portio, and preferably to be received at the formix vaginae.

The device according to the present invention is applicable for guiding, via the inlet and outlet ducts, a gaseous, liquid, solid, or suspended treatment substance to and from the cervical area for treating it in accordance with the method of this invention. Likewise it is applicable for filling a part of the chamber with a liquid, which in turn emits a gaseous therapeutic agent. Yet another application is to use one or more of the ducts for entering an instrument into the vagina for monitoring parts of the cervix, taking cell samples, flushing the treatment area with pharmaceuticals, etc. Further the cup of the device can be provided with the treatment substance in the form of an ointment, which emits a therapeutic agent.

Due to the chamber, which is obtained due to a gap between the bottom of the cup and the end of the portio, a volume is created where it is possible to circulate the treatment substance and thus to continuously provide the affected cells with fresh substance for the treatment. The gap is obtained by constructing the device such that the height of the wall is enough. The mouth of the cup by no means could get further up the vagina than to the formix cavity, and the distance from the formix cavity down to the end of the portio varies within a known interval from individual to individual. In order to cover the whole range of measures of said distance, which typically ranges from 20 to 50 mm, as well as the diameter of the portio, which typically ranges from 20–100 mm, some differently sized devices can be provided in practise.

Alternatively the device is arranged to be positioned at the cervix uteri of a human body, and comprises a cup, having a bottom and a wall attached to the bottom and extending therefrom, said wall having a mouth portion arranged to encircle the portio of the cervix uteri, and the height of the wall being such that, when the device is disposed at the cervix uteri, a chamber is defined by said bottom, said wall and said portio, said device further comprising a central pin, attached to the bottom and extending in the same direction as the wall.

This last mentioned structure of the device is primarily useful for the provision of a treatment substance in the cup followed by positioning the cup at the cervix uteri. In an embodiment thereof the cup is further provided with at least one inlet opening and at least one outlet opening for obtaining possibilities to provide the cup with the substance or to create a flow of substance through the cup after having positioned the device.

According to said alternative structure of the device there is a central pin, which similarly is provided according to an embodiment of the first mentioned structure, and which is arranged to cover the mouth of the cervical canal. This is to prevent, for example, a treatment substance from undesirably entering the cervical canal. However, in other embodiments of the device according to this invention the pin protrudes long enough to enter said canal in order to obtain a treatment also there.

Further embodiments of said device are provided with a supporting structure comprising a plurality of apertures, which supporting structure, depending on the existence and form of the pin, has somewhat different extensions. A main purpose of the supporting structure is to prevent the portio from extending too far down into the cup, while letting the substance, or the therapeutic agent thereof, into contact with the tissues. The portio could otherwise sink too low in the cup because the tissues are soft and moist. In conjunction with said prevention, the supporting structure, by means of said apertures, gives the treatment substance access to the area that is to be treated.

According to another embodiment of said device the pin is joined with the bottom of the cup and extends beyond the mouth of the cup to such an extent that the pin, when the device is positioned at the cervix area, extends at least a portion into the cervical canal. Further the pin is surrounded by a supporting structure comprising apertures. The main purpose of the supporting structure surrounding the pin is to prevent the cervical canal from collapsing onto the outer wall of the pin.

The device could additionally be used for administering conventional medicines and hold them for a predetermined time period. Per se, there is a known device for that specific purpose, as disclosed in an international patent application WO95/08363. This previously known device comprises a catheter having a closed end and an opening close to that end, and a disk or a funnel having a centre hole through which the catheter extends. When mounted at the cervix area, said closed end of the catheter is introduced into the cervix uteri for administering the pharmaceutical product within the cervix uteri. The disk or, alternatively, the funnel forms, as expressed in the publication, "a liquid-impervious seal" against the vaginal wall or the formix vaginae, respectively. However, this known device inter alia is not useable for letting in and out, respectively, a substance. Thus, inter alia it does not provide for the possibility of a continuous exchange of substance at the treatment area.

According to yet another embodiment of the inventive device it is provided with one or more sensors, which are used for monitoring and controlling parameters of interest for the treatment.

According to yet another aspect of the present invention it provides for the use of a substance comprising at least one of ozone, an ozone donor, oxygen, and an oxygen donor for the manufacture of a medicament for treating cells affected by an oncogenic virus. The medicament can be gaseous, liquid, solid or mixtures thereof.

Further objects and advantages of the present invention will be discussed below.

BRIEF DESCRIPTION OF THE DRAWINGS

Exemplifying embodiments of the invention will be described below with reference to the accompanying drawings, in which:

FIGS. 5 and 6 are schematic longitudinal and lateral, respectively, cross-sectional views of yet another embodiment of the device;

FIG. 11 is a schematic lateral cross-sectional view of another embodiment of the device;

FIG. 12 is a schematic longitudinal cross-sectional view of another embodiment of the device;

DESCRIPTION OF EMBODIMENTS

Figure 1:
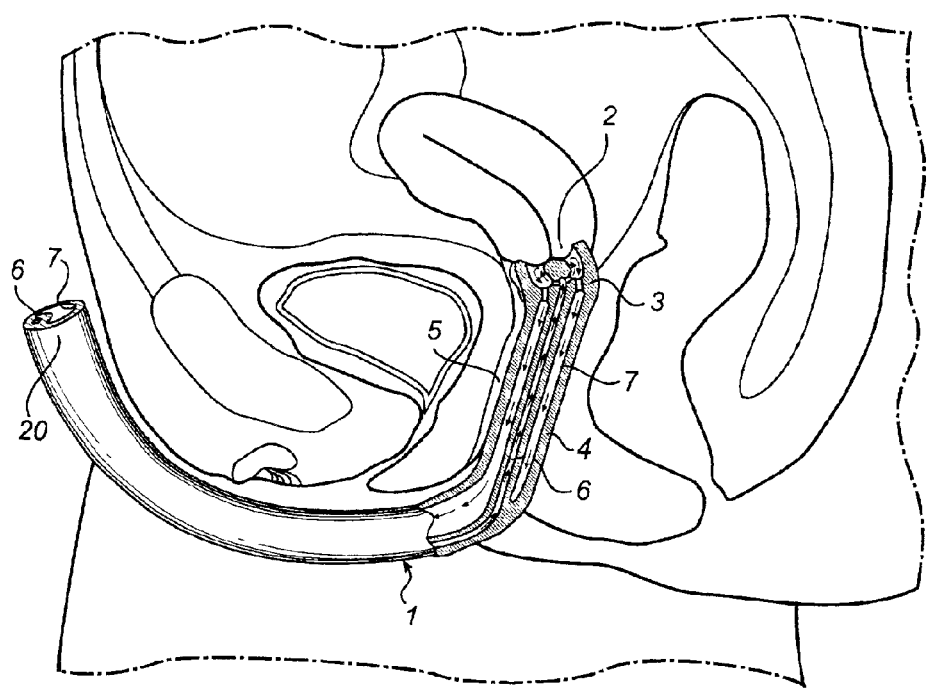
FIG. 1 is a schematic cross-sectional view of the device of the present invention positioned adjacent to the cervix of a woman.

In FIG. 1 the pelvis region of a human body is shown. A device 1, illustrated in a partly sectional view, according to an embodiment of the present invention is shown positioned at the cervix uteri 2, which below will also be referred to as the cervix. The device 1 comprises a cup, or cup portion, 3, and a shaft, or shaft portion, 4, connected to the cup 3 and extending to the exterior of the body. As shown in FIG. 1 the cup 3 is preferably inclined relative to the shaft so as to correspond to the anatomy of the vagina 5 and the cervix 2. The device has one, as in FIG. 1, or more inlet ducts 6 for supplying a gaseous, liquid, solid, or suspended substance to the cup 3, and one, as in FIG. 1, or more outlet ducts 7 for draining the cup 3 of said substance. In this embodiment the shaft 4 is a flexible tube, to such an extent that the shaft 4 can be bent but does not collapse when bent.

Figure 2:
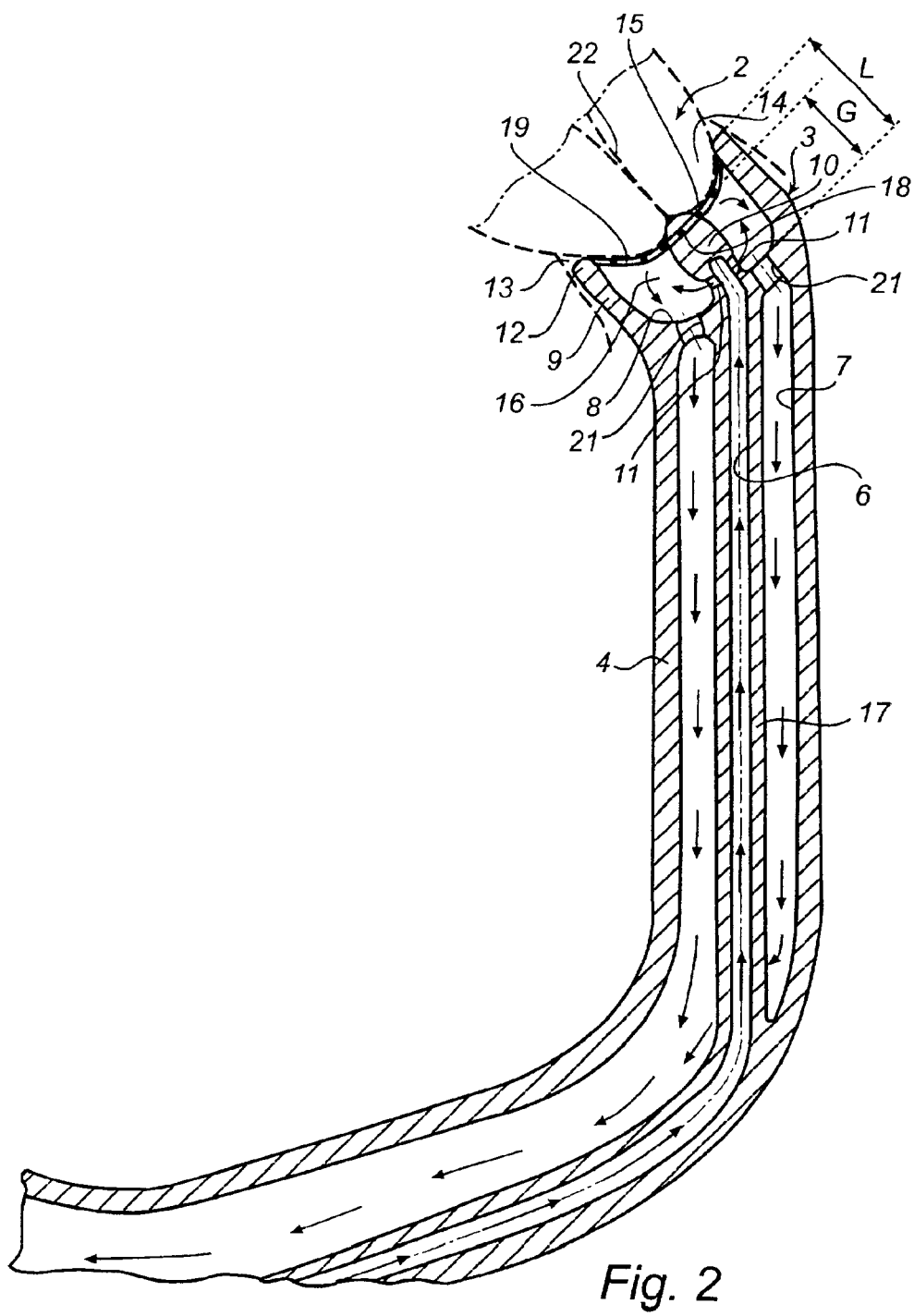
FIG. 2 is a schematic longitudinal cross-sectional view of an embodiment of the device.

This embodiment is shown in greater detail in FIG. 2. The same reference numerals are used throughout the figures for denoting equivalent or corresponding parts. As shown in FIG. 2 the cup 3 comprises a bottom 8 and a wall 9 attached to the bottom and extending therefrom. In this embodiment the wall is substantially cylindrical but other forms could be applicable too. In the figures the wall 9 extends upwards from the bottom 8, while the shaft 4, which likewise is connected to the bottom 8 extends in the opposite direction, i.e. downwards. The shaft can be detachably attached to the cup 3 so as to enable optional uses of the device as a mere cup or as a combination of cup 3 and shaft 4. The device as a whole can be manufactured as an integral part or in a plurality of parts, which are then assembled. In the latter case a modular system can be obtained, which system can comprise a plurality of varieties of each part. For example one or more the parts can be provided in several different sizes. Thereby various combinations of the parts can be made in order to customise the device for an individual.

Further, the cup 3 comprises a central pin 10 protruding upwards from the bottom 8 and covering the end of the cervical canal 22. The inlet duct 6 branches off into a plurality of branches at the base of the pin 10 and said plurality of branches 11 debouch, i.e. end, at said base. The wall 9 of the cup 3 ends with a mouth portion 12, which, when the device is in use, is received at the formix vaginae, or formix cavity, 13.

The wall 9 has a length (L) such that when the mouth portion 12 is properly positioned in the formix cavity 13, there is a gap (G) defined between the surface of the bottom 8 and the end 15 of the portio 14 of the cervix 2. In this way, a chamber 16 is defined inside the wall 9 of the cup 3 and the portio 15 that permits the circulation therein of a treatment substance.

As understood from above, the mouth portion 12 defines an opening that is dimensioned to enclose the cervix 2, and more specifically the portio 15 thereof. When the device is positioned in the vagina 5, at the cervix 2, the mouth portion 12 is firmly pushed towards the formix cavity 13. The wall 9 and the bottom 8 should therefore be semi-rigid, i.e. sufficiently rigid to maintain the chamber and not collapse due to an outside pressure on the cup 3, yet flexible enough to adjust to the cervix in order to provide a substantially sealed engagement with the wall of the cervix.

In this embodiment of FIG. 2 the inlet duct 6 is formed in the wall of the tubular shaft 4 except for a distance at the upper end of the shaft 4, where the inlet duct 6 branches off from the wall of the shaft 4 into a separate tube 17, which leads to the pin 10 and is attached to the bottom 8 of the cup 3. The bottom 8 is provided with a plurality of through holes 21, which are arranged around the end of the tube 17, and which interconnect the interior of the cup 3 with the outlet duct 7. It is to be noted that the substance flow could be reversed, i.e. the inlet duct can serve as the outlet duct and vice versa. As will be evident for the man skilled in the art by the following description, however, some minor modifications may then be necessary.

The cup is provided with a supporting structure 19, which in this and other herein disclosed embodiments is a grid. This is merely one of several possible realisations of the supporting structure. Other examples are a structure of spokes extending between the pin 10 and the wall 9, and a plate comprising elongated apertures. The grid can be constituted by, for example, a perforated plate or a net of strings. The grid 19 is attached in the wall 9 of the cup 3, close to the mouth thereof. The main function of the grid 19 is to support the portio 14 in order eliminate a risk that the portio 14 extends too far into the cup 3 and substantially reduces or even eliminates the volume of the chamber 16. The top 18 of the pin 10 protrudes through the grid 19. The length of the pin 10 is adapted to the length L of the wall 9 such that the top 18 of the pin 10 abuts the end of the cervical canal 22 at the end 15 of the portio 14, so as to prevent the treatment substance from entering the cervical canal 22.

The cup 3, the pin 10 and the grid 19, and the shaft 4 can be preassembled or can be loose parts that are combined as required from treatment to treatment.

Figure 9:
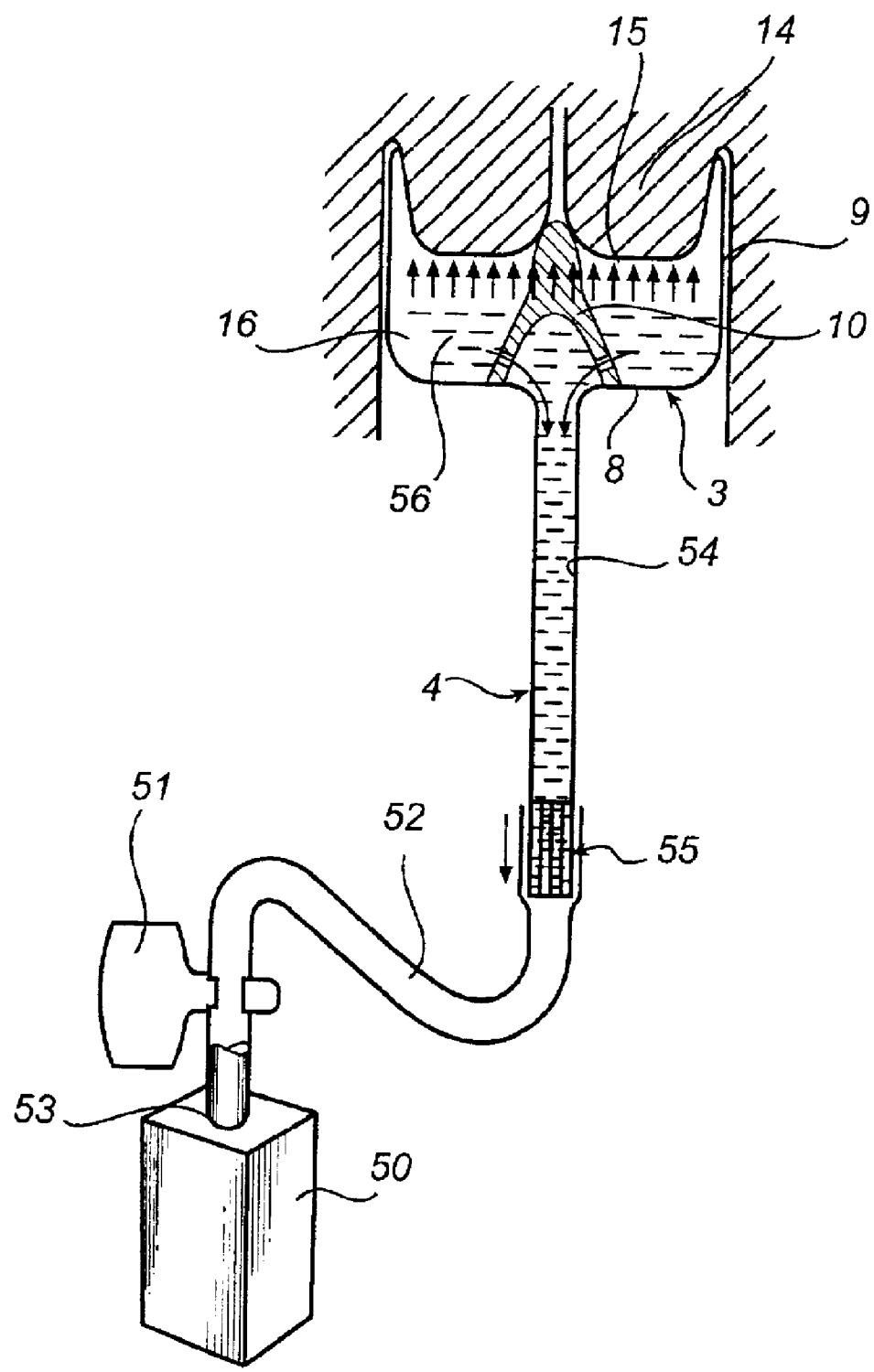
FIGS. 9 and 10 are partly cross-sectional, partly perspective schematic views of further embodiments of the device.

At the end 20 (FIG. 1) of the shaft 4, opposite to the end thereof which is joined with the cup 3, a substance source, such as shown in FIG. 9 at 50, can be connected. More particularly the source 50 can be connected to the inlet duct 6 for supplying a substance to the chamber 16, which will be further explained below. The flow of the supplied substance is regulated by means of a valve, such as the one shown in FIG. 9 at 51. For example, the source can be container having a pump for supplying the substance, or a gas bottle holding a gaseous substance under high pressure, or a bag holding a liquid substance for supplying the substance by means of gravitation.

In dependence of how the substance is input to the cup 3, it can be desired to, either merely lead the used substance out of the cup, or actively pump out the substance.

With reference to FIGS. 1–2, the cervical device 1 according to this embodiment of the present invention may be inserted into the vagina 5 of a female to introduce a suitable treatment gas, such as ozone ($O_3$), pure oxygen gas ($O_2$), an ozone donor, an oxygen donor, or a mixture of ozone and oxygen or a mixture with one or more further gases, for treating virus infected, precancerous and cancerous cells with the treatment gas. Ozone gas may kill viruses and inactivate them when the cells are subjected to the ozone gas, as thoroughly described in prior art. Oxygen has good healing effects on the human body as also thoroughly described in prior art, but could also have a similar or synergistic treatment effect. The pressure of the gas should be about one atmosphere, and possibly slightly higher, so that the ozone may get into contact with and cause a treatment effect on the cell membranes. The pressure of the gas should not be too high so that the gas destroys the cells and tissues in the vaginal cavity. Ozone is particularly useful for treating human papilloma viruses in cervical cancer and other virus caused cancer.

From the source 50 the gas is supplied to the chamber 16 via the inlet duct 6. When the gas flow arrives at the base of the pin 10 it is divided into sub-flows flowing through the branches 11, which thereby spred the gas equally, via the pin 10, over the end 15 of the portio 14, as shown by the arrows in FIG. 2. An overpressure in the chamber 16 is substantially avoided due to the larger total area of the outlet duct 7 than the total area of the inlet duct 6. The mouth portion 12 is sealingly tight inside the formix cavity 13 so that the treatment gas may not escape between the edge of the mouth portion 12 and the tissue. The sealing is obtained either substantially between the mouth portion 12 and the portio 14 of the cervix 2, or substantially between the mouth portion 12 and the vaginal wall of the formix region 13, depending on individual differences.

The seal also prevents any undesirable changes of the balance of the mucous membrane in the vaginal cavity because the mucous membrane is not exposed to the treatment gases if unwanted. However, in some cases it may be desired to treat also the vagina, wherein apertures can be provided along the inlet duct. It is also important that the cup 3 does not irritate the mucous membrane, that no mechanical cuts are performed and that no allergy causing materials are used. However, the cup 3 can be provided with retaining elements, such as knobs or the like, which contributes to holding the cup in place but which do not injure the tissue.

The gas is permitted to circulate in the chamber 16, as shown by the arrows and is then let out through the outlet duct 7. In this way, the pure and uncontaminated treatment gas flowing in the tube 17 enters into the chamber 16 through the valve 51, and the used or circulated treatment gas escapes into the space defined between the tube 17 and the inside wall of the shaft 4, i.e. the outlet duct 7. Of course there are possible alternatives to input the gas, some of which will make the valve 51 unnecessary. Further the outlet too can be provided with a valve, such as the output valve shown at 137 in FIG. 13. The output valve can be for example a throttle valve, any other pressure or flow regulating valve, controllable to maintain a sufficient pressure in the chamber 16 so that the treatment gas may penetrate through the cell membranes of the treated area.

The grid 19 further catches any lumpy secretion and prevents it from obstructing the branches 11 and the holes 21. The grid could additionally be manufactured so as to absorb, at least to some extent, said secretion.

The treatment gas may be particularly effective to treat light, moderate and severe cell-changes on the cervix. The development of progradiation to cancer on the cervix is usually, but not necessarily, a long process that may take up to 30 years. During this long process, the affected cells go through cell changes in stages. The undesirable and abnormal cell changes may be slowed down or stopped with the treatment method of the present invention. When the cells are treated effectively, the cell changes could be normalized so that the cells become healthy again. In other words, virus, and in particular Human papilloma virus, are inactivated, or destroyed. When inactivated the virus can not cause any (further) cell changes. At early stages of infection, the infection is treatable so as to prevent development of progradiation to cancer. This is favourable, in the light of the methods for virus detection presently at use. Treatable cell changes may also have occurred inside the cervical canal.

Other infections that are caused by other viruses in the same group as HPV may be treated with the treatment method of the present invention. Bacterial, fungal and other infections caused by micro-organisms in the cervix may be treated with the method and device of the present invention. One purpose of the treatment is to kill and inactivate the harmful viruses, such as HPV, in the cervical and the vaginal cavity. It may be advantageous to desiccate, i.e. dry out, cells that have gone through or are going through cell changes by means of dry gases. Another purpose of the treatment is to facilitate for the circulation of the treatment gases in the area that requires treatment while keeping it from reaching undesired areas. Additionally, the ozone/oxygen gas may be used to treat infertility that may be caused by bacteria and viruses. By using the treatment gas according to the present invention, the development of cervix cancer may be prevented and the normalization of dysplastic cells may be enhanced. The method of the present invention is not invasive and other forms of cancer that are caused by HPV or other oncogenic viruses, can be treated in the same way.

Figures 3, 4:
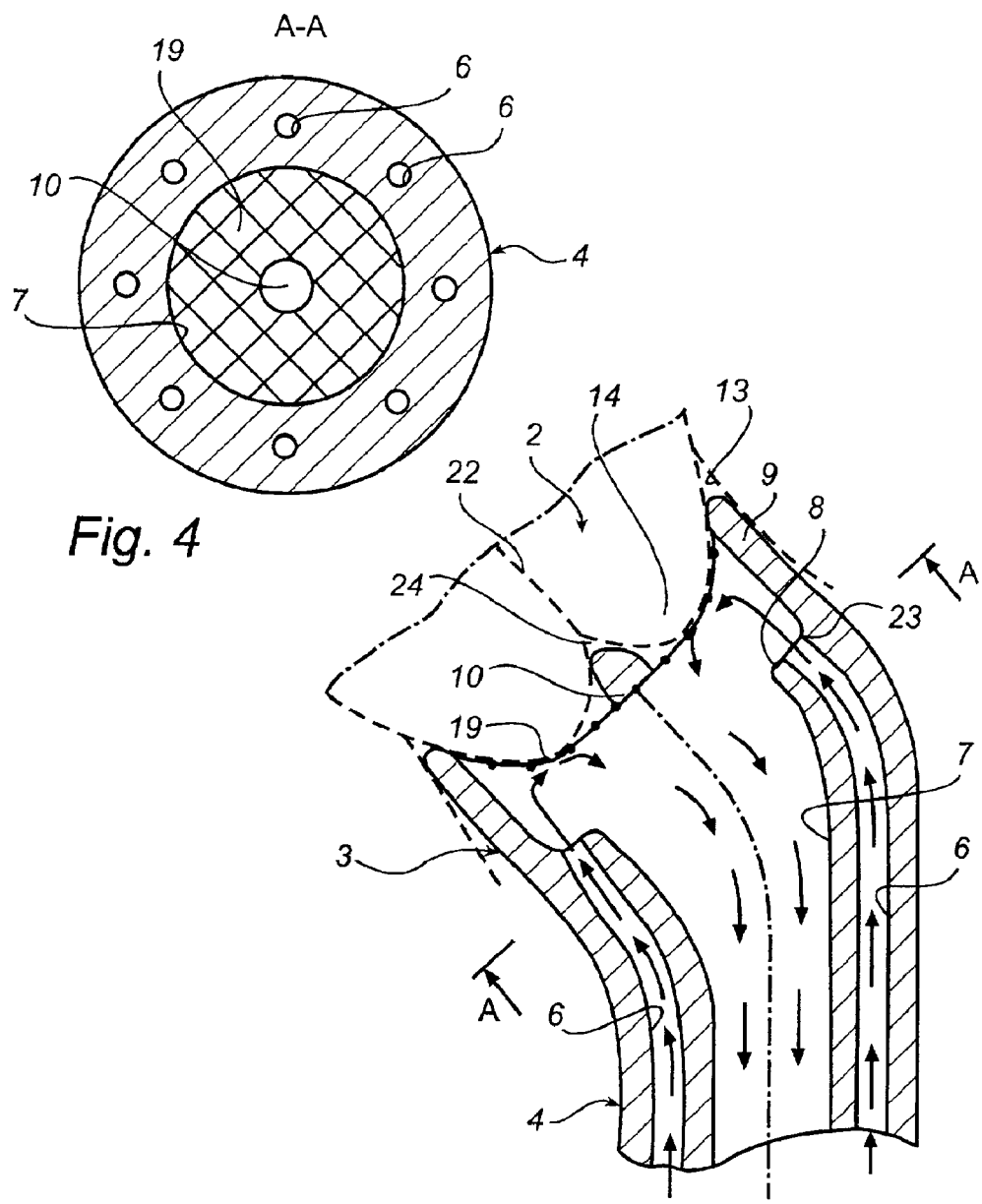
FIG. 3 is a schematic longitudinal cross-sectional view of another embodiment of the device.
FIG. 4 is a schematic lateral cross-sectional view of the embodiment of FIG. 3.

In FIGS. 3 and 4 another embodiment of the device is shown. It has several basic features in common with the embodiment described above. However, some differences are as follows. The inlet duct is provided as a plurality of ducts 6, which run in the wall of the tubular shaft 4 and end in the bottom 8 of the cup 3. Thus, the mouths 23 of the inlet ducts 6 are located close to the wall 9 of the cup 3. Further, the central pin 10 is supported by the grid 19. When the device is positioned in the vagina the top of the pin 10 abuts the portio 14 at the mouth 24 of the cervical canal 22. An upper portion of the pin 10 is approximately conical so as to better fit with the shape of the portio 14 close to the mouth 24 of the cervical canal 22. The pin 10 can be substantially smaller than the one shown in FIG. 4. As a border case, it will even be possible to simply provide the grid 19 with a central portion being impervious, where the thickness of the central portion does not exceed the thickness of the grid 19. The bottom 8 of the cup 3 in this embodiment is a mere shelf extending from the inner side of the wall 9 of the cup to the inner side of the wall of the shaft 4, the latter wall being thicker than the wall 9 of the cup 3. This means that the centre of the shaft 4 consists of a single outlet duct 7.

Yet another embodiment of the device is shown in FIG. 5 and FIG. 6. In the previous embodiments the length and the position of the top of the central pin 10 in relation to the mouth, i.e. the very edge of the mouth portion 12, of the cup 3 were adapted to the geometry of a typical cervix such that the pin 10 abutted the portio 14. In this embodiment the central pin 10 is rather substantially longer such that it extends into the cervical canal 22, and it even extends along the whole length of the cervical canal 22. A top portion 25 of the pin 10 protrudes into the uterus cavity 26. The top portion 25 is provided with a retaining portion 27, which is a circumferencial flange, or rim, protruding radially from the pin 10. The flange 27, when the device is positioned in the vagina at the cervix area, rests on the inner wall of the uterus cavity 26. Thereby the flange contributes to the retaining of the device and delimits the area of treatment. This embodiment has the additional function of enabling treatment of the illness in the cervical canal 22. Consequently the inlet duct 6 extends along the centre of the pin 10 and radial branches 28 extend from the inlet duct 6 to the surface of the pin 10. The pin 10 has a central shaft 29 provided with longitudinal flanges 30, which protrude radially. The longitudinal flanges 30 are arranged equidistantly around the pin 10. The branches 28 debouch between the longitudinal flanges 30. The grid 19 in this embodiment surrounds the pin 10, and thus the flanges 30. Thereby the flanges 30 and the grid 19 cooperates in widening the cervical canal and forming a spacing between the surface of the cervical canal 22 and the surface of the central shaft 29 of the pin 10. Thereby the gas is easier let out of the branches 28 of the inlet duct 6. Even if the inlet duct 6 does not debauch in the chamber 16 the surface area of the portio 14 is still being treated, by the gas returning from the cervical canal 22 into the chamber 16 before flowing out through the outlet duct 7.

Figures 7, 8:
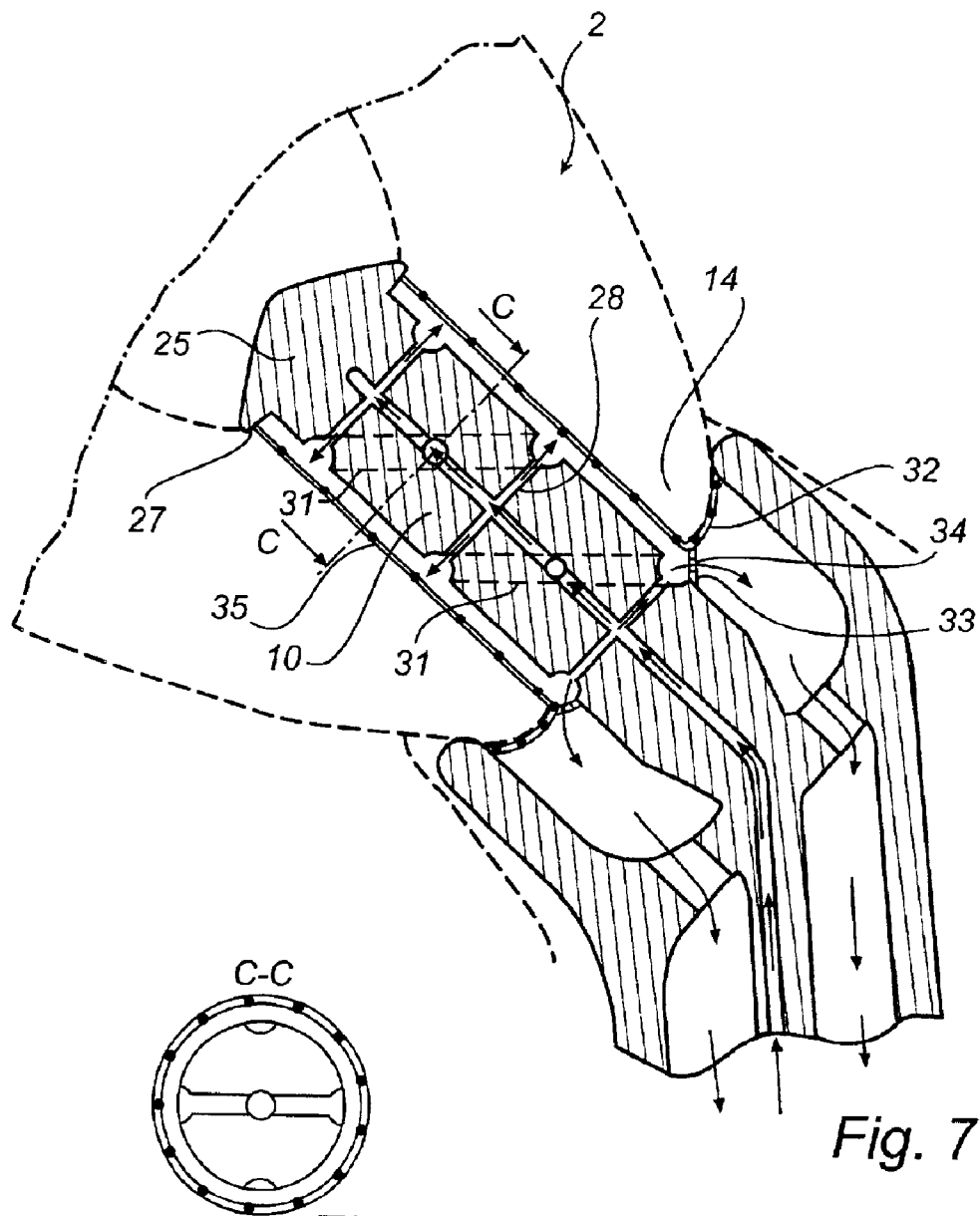
FIGS. 7 and 8 are schematic longitudinal and lateral, respectively, cross-sectional views of still another embodiment of the device.

A modification of the embodiment of FIGS. 5–6 is shown in FIG. 7 and FIG. 8. In this embodiment as well the pin 10 extends through the cervical canal 22 and is provided with the inlet duct 6 at the centre thereof and branches extending radially from the inlet duct 6. However, in the preceding embodiment there are four branches at each point of ramification, while in this embodiment there are two. At two neighbouring ramifications the branches extend perpendicular to each other. In order to obtain the spacing between the pin 10 and the cervical canal 22 rather than flanges the pin 10 is provided with recesses 31 running helically along the length of the pin 10. The recesses are wider than the branches 28 and the branches 28 end in the bottom area of the recesses 31. Additionally the grid 19 is mounted so as to provide a distance between the grid 19 and the outer wall of the pin 10. The grid 19, in this embodiment, comprises a lower portion 32, which extends substantially radially outwards of the pin 10 and is attached to the wall 9 of the cup 3, and an upper portion 35, which extends between an inner edge of the lower portion 32 and the flange 27 of the pin 10. Approximately at the lower end of the upper portion 35 a support structure, here a support ring 33, is arranged. The support ring 33 is attached to the pin 10 and to the grid 19, and it has several holes 34 letting the substance out of the space between the pin 10 and the wall of the cervical canal 22 and into the cup 3. Preferably, the grid 19, like in the embodiment described above, is preformed such that it approximately adapts to the form of the end 15 of the portio 14. Structural details such as number of branches at each ramification, the number of helical recesses, etc. can be widely modified within the scope of this invention.

As mentioned above the treatment substance can be supplied directly as a gas, or the therapeutic agent can be dissolved in water, or any other suitable liquid or medium such as ice cubes and solid substances. Further the substance, rather than the very treatment agent, can contain a donor, which can be supplied in a suitable form, wherein the therapeutic agent is then generated in situ. The substance can then be circulated past the exposed area around the cervix and the cervical canal, either at a distance from the tissue or in contact therewith. However, in some cases it is not necessary to circulate the substance. It can simply be fed to the chamber 16 of the cup 3 and be held there during the treatment period. In FIG. 9 there is shown, most schematically, an embodiment of the device 1, which is adapted to providing a liquid or a suspension to the chamber 16 and retaining it there for a period of time. The device comprises a source 50 of the substance, which source comprises a pump (not explicitly shown), and a hose 52 attached to an outlet 53 of the source 50. The hose 52 is connected to the shaft 4. The hose is provided with a valve 51. The cup 3 constitutes of a bottom 8 and a wall 9. There is a central pin 10. The shaft is tubular and comprise a single duct 54. The connection between the hose 52 and the shaft 4 is reciprocatable. After having filled the chamber 16 with the liquid to such a level that there remains an air gap between the surface of the liquid and the end 15 of the portio 14 the valve 51 is closed and the hose 52 is slightly withdrawn at the connection 55. Since the chamber 16 is sealed this movement creates an underpressure therein, which contributes to the retaining of the cup, and which facilitates the emission of ozone from the substance.

Figure 10:
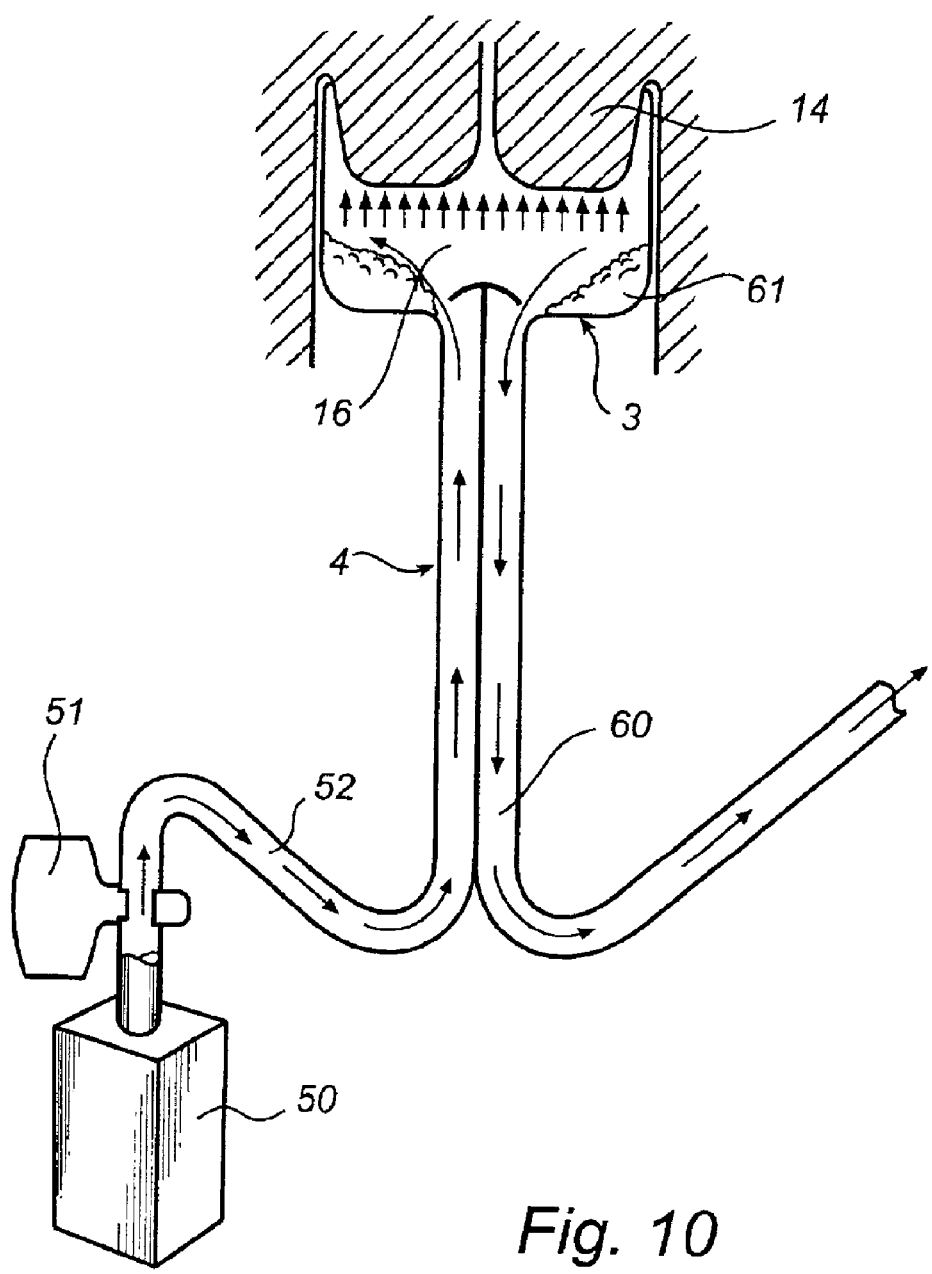

It may also be possible to locally treat cervical cancer by permitting the treatment gas to be chemically released from a solid state material, such as a piece of cotton or textile fabric, that is applied at the portio, or into the cervical canal. This is illustrated in FIG. 10. The material 61 is applied in the cup 3 at the bottom thereof. A pure gas or a gas mixture is provided to the cup 3 from a source 50 through an inlet duct 52, and guided out of the cup 3 through an outlet duct 60, in order to ventilate the chamber 16 of the cup 3 so as to keep the concentration of the treatment gas, e.g. ozone, at an appropriate level. The gas flow is controlled by means of a valve 51.

The shaft 4 may be relatively stiff to make sure the cup 3 is properly held in place in the vaginal cavity. Of course, the shaft 4 may also be relatively soft that is more comfortable for the wearer. The shaft 4 may have a plurality of openings 113 defined therein, as shown most schematically in FIG. 11, to promote the disposal of the treatment gas that has been circulated in the chamber 16 and to possibly treat portions of the inside wall of the vaginal opening. The shaft 4 may have a curved outer wall 110, so that a chamber 111 may be formed between the shaft 4 and the inner wall 112 of the vaginal opening so that the gas that leaks out through the openings may circulate between the shaft 4 and said inner wall 111. The shaft 4 should be sufficiently stiff so that the chamber 16 may be maintained despite a pressure from the vaginal side walls. The shaft 4 may also have a smooth outer surface.

The source 50 comprises a container that contains the gas under a pressure that is higher than the pressure outside the container and inside the chamber 16. The container may be made very small so that the container may be held inside the underwear or the clothes of the person to be treated.

In FIG. 12 yet another embodiment of the device is shown, wherein the shaft is realised by means of separate tubes, one for each inlet duct 120 and outlet 121 duct respectively.

Figure 13:
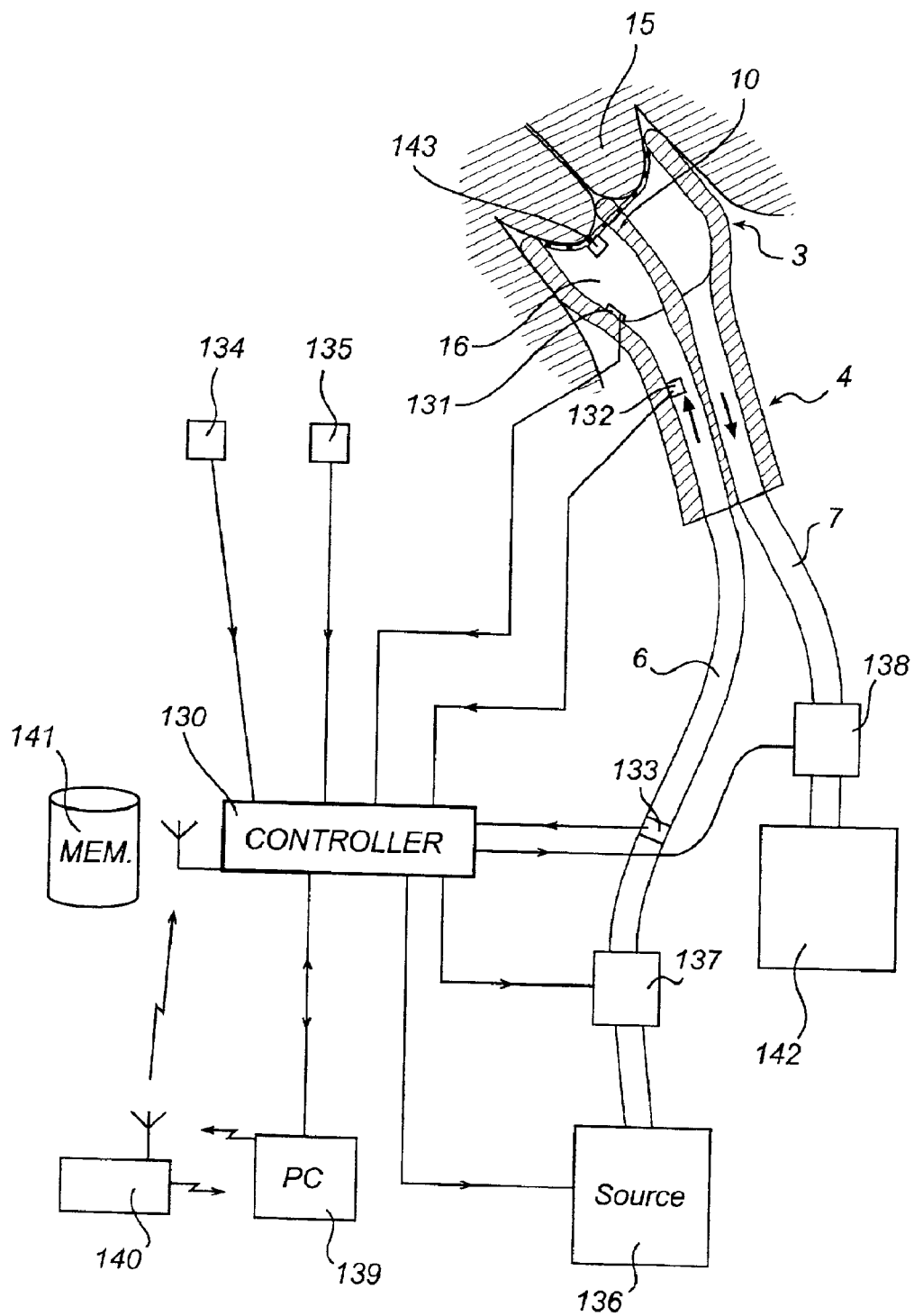
FIG. 13 in a schematic block diagram shows monitoring and control equipment of the device.
Figure 14:
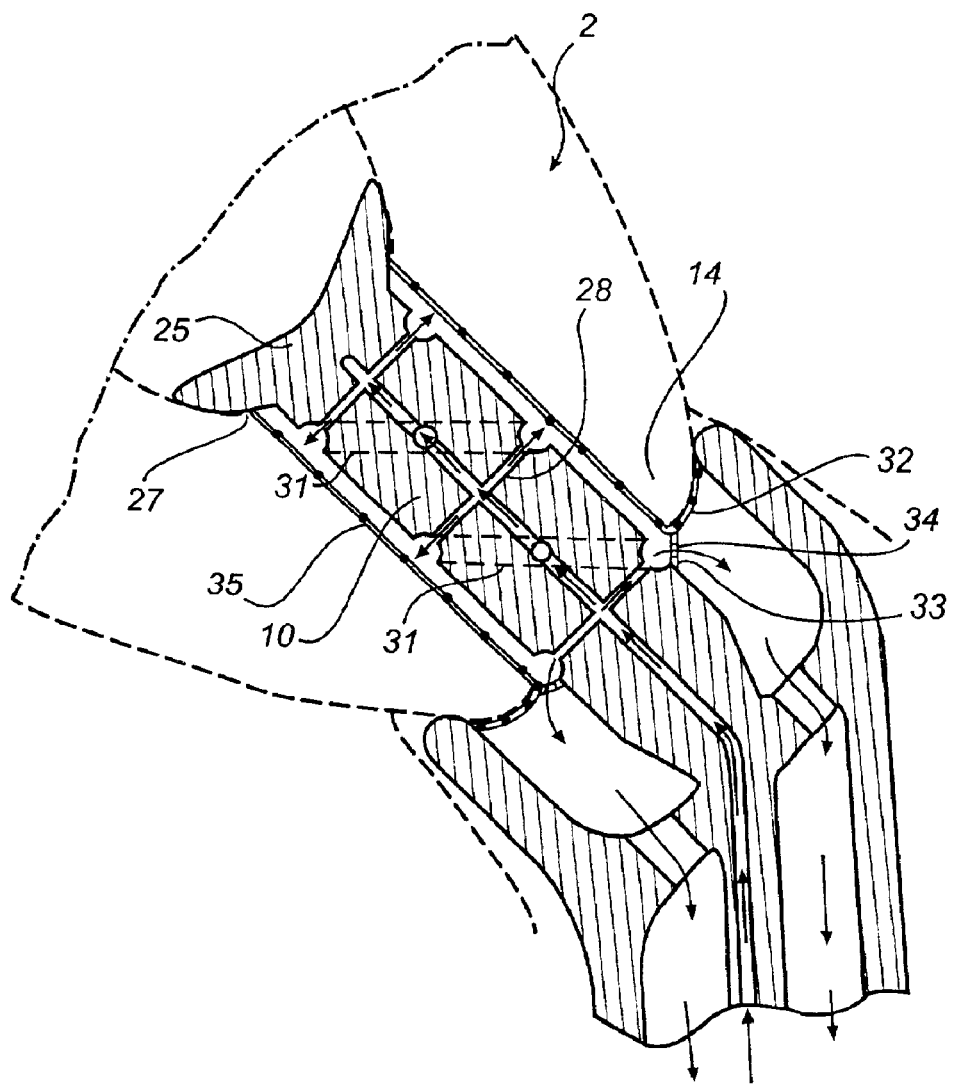
FIG. 14 is a schematic longitudinal cross-sectional view of another embodiment of the device according to the present invention.

The device is preferably provided with means for monitoring and controlling the treatment, as shown in FIG. 13. The device of FIG. 13, in addition to the cup 3, the shaft 4, the inlet and outlet ducts 6, 7 respectively, a source of the substance 136, an inlet valve 137, and an outlet valve 138, comprises a controller 130, at least one and preferably a plurality of sensors 131–135, a memory 141, a PC 139, and a wireless control and display unit 140. The sensors 131–135, the memory 140, the PC 139, and the wireless unit 140 are connected to the controller 130. The PC and the controller can be provided with application specific software for performing the monitoring and control. The sensors 131–135 can be provided at various places, for example in the cup 3, in the inlet and/or outlet ducts 6, 7, or at other places of the body. Additionally sensors, such as sensor 143, can be arranged so as to abut the body tissue at the treatment area. The sensors 131–135, 143 can be of various types, such as sensors measuring time, temperature, pressure, pH, flow, humidity, pulse, gas concentration, conductivity, etc. Different techniques can be used such as biomonitoring, imaging, ion selective electrodes, etc.

The signals of the sensors 131–135, 143 are fed to the controller 130, which in dependence thereof controls the treatment process by supplying a therapeutic agent in a predetermined dosage, and at a predetermined duration, repetition etc. In order to obtain the desired properties at the area where the affected cells are located, the controller can for example control the inlet valve 137 in order to control the gas or liquid flow, control the outlet valve 138 in order to control the pressure in the chamber 16, etc. The controller 130, in turn, can be provided with control information and instructions from the PC, and the treatment can also be supervised by means of the PC. The wireless unit 140 can be used to obtain a freedom of movement for the patient being treated as well as for the person performing the treatment.

The device according to this invention is preferebly portable so that the patient can move around. For example the device can include the functionality of a cellular phone or a bluetooth apparatus.

The length and repetitiveness of the treatment are chosen in dependence of the present circumstances.

The method and device of the present invention may also be used in the case that, after all, conventional surgery has already been used on the cervix uteri. Then the invention is applicable for post-treatment of cancerous cells that could not be removed through the conventional surgery. Thereby the risk of reoccurrence of the cancer growth is reduced or prevented.

Above a few embodiments of the device and method according to the present invention have been described. These should be seen as merely non-limiting examples. Many modifications will be possible within the scope of the invention as defined by the claims.

What is claimed is:

1. A non-invasive method for treating cells affected by at least one oncogenic virus, comprising the steps of:

providing a substance comprising at least one of ozone, an ozone donor, oxygen and an oxygen donor; and subjecting an area of body tissue comprising said affected cells to said substance wherein said step of subjecting comprises the steps of:

guiding said substance to said area;

treating said affected cells by means of said substance; and guiding used substance away from said area wherein said area of body tissue constitutes at least a portion of a cervix uteri that can be affected by oncogenic viruses and wherein said cells constitute epithelial cells.

2. A method according to claim 1, wherein said oncogenic virus is Human Papilloma Virus.

3. A method according to claim 1, further comprising the step of desiccating said affected cells by means of said substance.

4. A method according to claim 3, wherein said area is the portio of the cervix uteri.

5. A method according to claim 3, wherein said area is the inside of the cervical canal of the cervix uteri.

6. A method according to claim 1, wherein said substance is a liquid or a solid or a mixture thereof, further comprising the steps of:

providing a substance holder with said substance; and positioning said substance holder at said area.

7. A method according to claim 6, further comprising the steps of:

sealingly enclosing said area by means of said substance holder such that a chamber is defined by said substance holder and said body tissue of said area; and creating an underpressure within said chamber.

8. A method according to claim 1, further comprising the step of monitoring parameters indicating status and progression of the treatment.

9. A method according to claim 8, further comprising the step of controlling said parameters.

10. A method according to claim 8, said parameters being selected from the group consisting of concentrations, substance flow, conductivity, humidity, pulse, pressure at said area, duration of the treatment, temperature at said area, pH at said area, and break down products at said area.

11. A method according to claim 9, wherein said step of controlling is remotely performed.

12. A method according to claim 1, further comprising the step of pumping said substance away from said area.

13. A method according to claim 1, said step of treating comprising the step of bringing said substance into contact with said area of body tissue.

14. A method according to claim 1, further comprising the step of providing a device for accomplishing said treatment
  wherein said device is arranged to be positioned at the cervix uteri of a human body, the device comprising a cup, having a bottom and a wall attached to the bottom and extending therefrom, and a shaft connected at one end thereof to the bottom and extending in an opposite direction of the wall, said shaft comprising at least one inlet duct and at least one outlet duct, said wall having a mount portion arranged to encircle the portio of the cervix uteri, a chamber is defined by said bottom, said wall and said portio, said outlet duct having at least one opening within said chamber.

15. A non-invasive method for treating cells infected by at least one of pathologic viruses, bacteria and fungi in a uterus cavity or an uterine tube, comprising the steps of:
  providing a substance comprising at least one of ozone, an ozone donor, oxygen and an oxygen donor; and
  subjecting at least an area of said uterus cavity or uterine tube comprising said affected cells to said substance further comprising the steps of:
  guiding said substance into the uterus cavity;
  treating said affected cells by means of said substance; and
  guiding used substance away from said uterus cavity.

* * * * *